(12) United States Patent
Forshee et al.

(10) Patent No.: US 9,222,043 B2
(45) Date of Patent: Dec. 29, 2015

(54) DIPYRROMETHENES AND AZADIPYRROMETHENES AS MARKERS FOR PETROLEUM PRODUCTS

(75) Inventors: Philip B. Forshee, McKinney, TX (US); Greg R. Hundt, Dallas, TX (US); Jeffrey L. Conroy, Allen, TX (US)

(73) Assignee: Authentix, Inc., Addison, TX (US)

( * ) Notice: Subject to any disclaimer, the term of this patent is extended or adjusted under 35 U.S.C. 154(b) by 472 days.

(21) Appl. No.: 12/885,741

(22) Filed: Sep. 20, 2010

(65) Prior Publication Data

US 2011/0069307 A1    Mar. 24, 2011

Related U.S. Application Data

(60) Provisional application No. 61/244,525, filed on Sep. 22, 2009.

(51) Int. Cl.
*G01N 33/26* (2006.01)
*C10L 1/00* (2006.01)
*G01N 33/28* (2006.01)
*C10L 1/30* (2006.01)
*C10L 1/182* (2006.01)
(Continued)

(52) U.S. Cl.
CPC .................. *C10L 1/003* (2013.01); *C10L 1/303* (2013.01); *G01N 33/28* (2013.01); *C10L 1/1824* (2013.01); *C10L 1/1852* (2013.01); *C10L 1/232* (2013.01)

(58) Field of Classification Search
CPC .... G01N 33/2882; G01N 33/28; C10L 1/003; C10L 1/303
USPC ............................................ 356/300; 436/56
See application file for complete search history.

(56) References Cited

U.S. PATENT DOCUMENTS 4,221,593 A    9/1980 Kubo
4,774,339 A *  9/1988 Haugland et al. ............. 548/405
(Continued)

FOREIGN PATENT DOCUMENTS

EP    0786498    7/1997
EP    0806460    11/1997
(Continued)

OTHER PUBLICATIONS

Yu et al., "Mono- and Di(dimetylamino)styryl-Substituted Borondipyrromethene and Borondiindomethene Dyes with Intense Near Infrared Fluorescence", 2006, Wiley InterScience, pp. 176-187.*
(Continued)

*Primary Examiner* — Kara E Geisel
(74) *Attorney, Agent, or Firm* — Conley Rose, P.C.; Rodney B. Carroll

(57) ABSTRACT

Marking a petroleum product includes adding a covert dye selected from the group consisting of azadipyrromethene dyes, dipyrromethene dyes, and any combination thereof to the petroleum product and distributing the dye in the petroleum product. A petroleum product selected for analysis may be spectroscopically analyzed for the presence of an azadipyrromethene dye, a dipyrromethene dye, or a combination thereof. A concentration of at least one azadipyrromethene or dipyrromethene dye present in the portion of the petroleum product may be determined to identify the petroleum product as counterfeit, adulterated, or authentic based on the determined concentration of the azadipyrromethene or dipyrromethene dye.

26 Claims, 13 Drawing Sheets

(51) Int. Cl.
*C10L 1/185* (2006.01)
*C10L 1/232* (2006.01)

(56) References Cited

U.S. PATENT DOCUMENTS

| | | | |
|---|---|---|---|
| 5,187,288 A * | 2/1993 | Kang et al. | 548/110 |
| 5,248,742 A | 9/1993 | McGarry et al. | |
| 5,248,782 A | 9/1993 | Haugland et al. | |
| 5,324,567 A | 6/1994 | Bratchley et al. | |
| 5,525,516 A * | 6/1996 | Krutak et al. | 436/56 |
| 5,661,035 A * | 8/1997 | Tsien et al. | 436/63 |
| 5,710,046 A * | 1/1998 | Rutledge et al. | 436/56 |
| 5,718,754 A | 2/1998 | Macpherson et al. | |
| 5,723,218 A * | 3/1998 | Haugland et al. | 428/402 |
| 5,723,338 A * | 3/1998 | Rutledge et al. | 436/56 |
| 5,804,447 A * | 9/1998 | Albert et al. | 436/56 |
| 5,853,464 A | 12/1998 | Macpherson et al. | |
| 5,935,755 A | 8/1999 | Kazmaier et al. | |
| 5,958,780 A * | 9/1999 | Asher et al. | 436/56 |
| 6,008,888 A | 12/1999 | Nottke et al. | |
| 6,060,324 A * | 5/2000 | Naguib | 436/71 |
| 6,155,605 A | 12/2000 | Bratchley et al. | |
| 6,259,506 B1 | 7/2001 | Lawandy | |
| 6,275,285 B1 | 8/2001 | Nottke et al. | |
| 6,306,628 B1 * | 10/2001 | Rothschild et al. | 435/91.3 |
| 6,344,272 B1 | 2/2002 | Oldenburg et al. | |
| 6,514,767 B1 | 2/2003 | Natan | |
| 6,608,670 B2 | 8/2003 | Nottke et al. | |
| 6,610,351 B2 | 8/2003 | Shchegolikhin et al. | |
| 6,685,986 B2 | 2/2004 | Oldenburg et al. | |
| 6,861,263 B2 | 3/2005 | Natan | |
| 6,991,914 B2 * | 1/2006 | Park et al. | 435/19 |
| 7,192,778 B2 | 3/2007 | Natan | |
| 7,220,732 B2 | 5/2007 | O'Shea et al. | |
| 2001/0001569 A1 | 5/2001 | Lawandy | |
| 2002/0025490 A1 | 2/2002 | Shchegolikhin et al. | |
| 2002/0048013 A1 | 4/2002 | Nottke et al. | |
| 2003/0166297 A1 | 9/2003 | Natan | |
| 2003/0180769 A1 * | 9/2003 | Metzker | 435/6 |
| 2004/0058058 A1 | 3/2004 | Shchegolikhin et al. | |
| 2004/0203159 A1 | 10/2004 | Zander et al. | |
| 2005/0206892 A1 | 9/2005 | Wang et al. | |
| 2005/0217424 A1 | 10/2005 | Natan | |
| 2005/0219509 A1 | 10/2005 | Natan | |
| 2005/0221494 A1 | 10/2005 | Natan | |
| 2005/0255599 A1 | 11/2005 | Wang et al. | |
| 2005/0272160 A1 | 12/2005 | Natan | |
| 2005/0287618 A1 * | 12/2005 | Haugland et al. | 435/7.92 |
| 2006/0038979 A1 | 2/2006 | Natan et al. | |
| 2006/0152706 A1 | 7/2006 | Butland | |
| 2007/0165209 A1 | 7/2007 | Natan et al. | |
| 2008/0102534 A1 | 5/2008 | Ulrich et al. | |
| 2008/0118982 A1 * | 5/2008 | Forshee et al. | 436/56 |
| 2008/0149850 A1 | 6/2008 | Tardif et al. | |

FOREIGN PATENT DOCUMENTS

| | | |
|---|---|---|
| EP | 1156459 | 2/2002 |
| EP | 0898768 | 7/2002 |
| EP | 2427685 | 1/2009 |
| WO | WO 91/11492 | 8/1991 |
| WO | WO 91/11703 | 8/1991 |
| WO | WO 97/39428 | 10/1997 |
| WO | WO 00/55586 | 9/2000 |
| WO | WO 01/38858 | 5/2001 |
| WO | WO 02/085543 | 10/2002 |
| WO | WO 2005/040739 | 5/2005 |
| WO | WO 2005/114152 | 12/2005 |
| WO | WO 2006/058448 | 6/2006 |
| WO | WO 2006/086008 | 8/2006 |

OTHER PUBLICATIONS

Ulrich et al., "The Chemistry of Fluorescent Bodipy Dyes: Versatility Unsurpassed", 2008, Wiley InterScience, pp. 1184-1201.*

Louder et al., "Functionalized $BF_2$ chelated azadipyrromethene dyes," Tetradedron, 64, Feb. 3, 2008, pp. 3642-3654.

O'Shea et al., "Synthesis of $BF_2$ chelates of tetraarylazadipyrromethenes and evidence for their photodynamic therapeutic behaviour," Chem. Commun., Jul. 23, 2002, pp. 1862-1863.

Zhao et al., "Conformationally Restricted Aza-BODIPY: Highly Fluorescent, Stable Near-Infrared Absorbing Dyes," Chem. Eur. J., Jul. 19, 2006, 12, pp. 7254-7263.

Loudet et al., "BODIPY Dyes and Their Derivatives: Syntheses and Spectroscopic Properties," Chem. Rev., Oct. 9, 2007, 107, pp. 4891-4932.

Gabe et al., "Highly Sensitive Fluorescence Probes for Nitric Oxide Based on Boron Dipyrromethene Chromophore-Rational Design of Potentially Useful Bioimaging Fluorscence Probe," J. Am. Chem. Soc., Feb. 19, 2004, 126, pp. 3357-3367.

Gorman et al., "In Vitro Demonstration of the Heavy-Atom Effect for Photodynamic Therapy," J. Am. Chem. Soc., Aug. 10, 2004, 126, 34, pp. 10619-10631; Supporting Information, pp. S1-S69.

Burghart et al., "3,5-Diaryl-4,4-difluoro-4bora-3a,4a-diaza-s-indacene (BODIPY) Dyes: Synthesis, Spectroscopic, Electrochemical, and Structural Properties," J. Org. Chem., Sep. 30, 1999, 64, pp. 7813-7819.

Chen et al., "4,4-Difluoro-4-bora-3a,4a-diaza-s-indacene (BODIPY) Dyes Modified for Extended Conjugation and Restricted Bond Rotations," J. Org. Chem., Apr. 18, 2000, 65, pp. 2900-2906.

Hall et al., "A Modular Synthesis of Unsymmetrical Tetraarylazadipyrromethenes," J. Org. Chem., Jun. 15, 2005, 70, pp. 5571-5578.

Li et al., "Syntheses and Spectral Properties of Functionalized, Water-Soluble BODIPY Derivatives," J. Org. Chem., Feb. 14, 2008, 73, pp. 1963-1970.

Loudet et al., "B,O-Chelated Azadipyrromethenes as Near-IR Probes," Organic Letters, Sep. 25, 2008, 10 (21), pp. 4771-4774; Supplementary Information, S1-S49.

International Search Report and the Written Opinion of the International Searching Authority, PCT/US2010/049597, mailed Dec. 15, 2010.

Briggs, Jr. et al., "Dual-Wavelength Absorption Imaging of Diesel Sprays," Paper ID IClass06-135, Aug. 27-Sep. 1, 2006, 7 pages.

Foreign communication from a related counterpart application—Examination Report, Canadian application No. 2,773,774, Mar. 26, 2013, 2 pages.

* cited by examiner

US 9,222,043 B2

DIPYRROMETHENES AND AZADIPYRROMETHENES AS MARKERS FOR PETROLEUM PRODUCTS

CROSS REFERENCE TO RELATED APPLICATIONS

This application claims priority from U.S. Provisional Patent Application Ser. No. 61/244,525 filed on Sep. 22, 2009, which is incorporated herein by reference.

TECHNICAL FIELD

The present invention relates to covert marking of petroleum products with a dipyrromethene dye, an azadipyrromethene dye, or any combination thereof.

BACKGROUND

The problems of counterfeit petroleum products are widespread and well documented. Branded products, which possess favorable properties over competitors, are imitated for commercial gain. These counterfeit products may appear visually identical to the consumer as the branded product, but may lack favorable properties afforded through the addition of proprietary chemical additives. Moreover, significant commercial gain may also occur through the adulteration of a branded product with, for example, a readily available commercial solvent. As such, the ability to distinguish a genuine product or the dilution of such from imitations is valuable.

Another consideration arises from the identification and quantification of chemical additives. Chemical additives are important constituents of some oil-based products such as gasoline, diesel fuel, lubricating oils, and the like. The additives are designed to impart favorable chemical properties to a product such that their absence or reduction may result in a significant loss of performance of the product in question. These additives can be introduced at a central distribution point into products that may be distributed worldwide. As the performance of the product is often related to the quantity of chemical additive introduced into the final retailed product, a system capable of monitoring the additive at any point of the supply chain is advantageous.

DETAILED DESCRIPTION

One or more azadipyrromethene dyes, dipyrromethene dyes, or any combination thereof may be added as direct-read near-infrared markers to a fluid petroleum product in an amount between about 0.1 ppb and about 10,000 ppb. As used herein, "direct read" generally refers to a marker that is detectable in a fluid petroleum product without sample preparation, such as chemical extraction, reaction, or the like. The markers may be used as covert dyes to identify and separate batches of petroleum products, analyze fluid flow, and detect leakage or dilution. As used herein, "covert dye" generally refers to a dye that is invisible to the human eye. That is, a petroleum product marked with a covert dye is visually indistinguishable from an unmarked petroleum product. Petroleum products to be marked may include, for example, gasoline, diesel fuel, biodiesel fuel, kerosene, liquefied petroleum gas (LPG), and industrial solvents, such as ethanol, hexane, toluene, xylenes, naptha, aromatic solvents (100, 150, 200, etc.), aliphatic solvents (C6, C9, etc.), mineral oil, and the like. The presence of an azadipyrromethene or dipyrromethene marker may be determined by fluorescence spectroscopy, absorbance spectroscopy, or both.

Figure 1A:
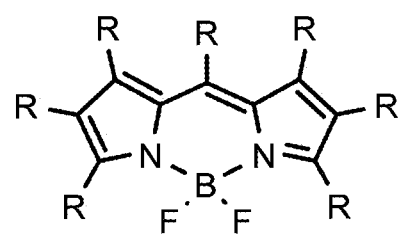
FIG. 1A illustrates general structure of a dipyrromethene dye.
Figure 1B:
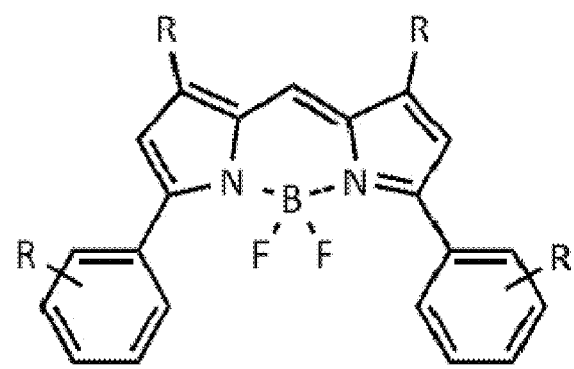
FIG. 1B illustrates general structure of a dipyrromethene dye.
Figure 1C:
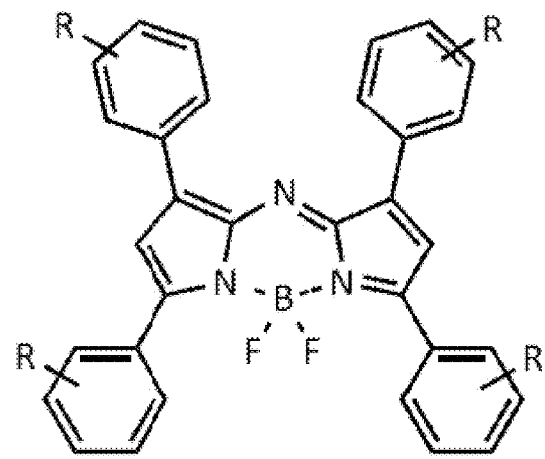
FIG. 1C illustrates general structure of an azadipyrromethene dye.
Figure 1D:
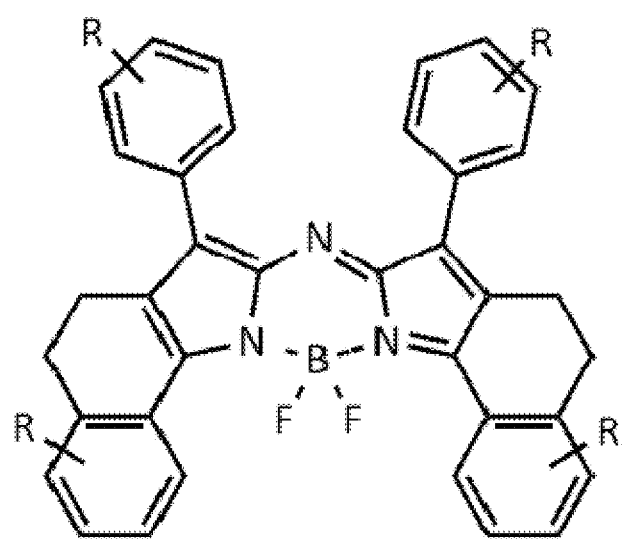
FIG. 1D illustrates a general structure of a conformationally restricted azadipyrromethene dye.
Figure 1E:
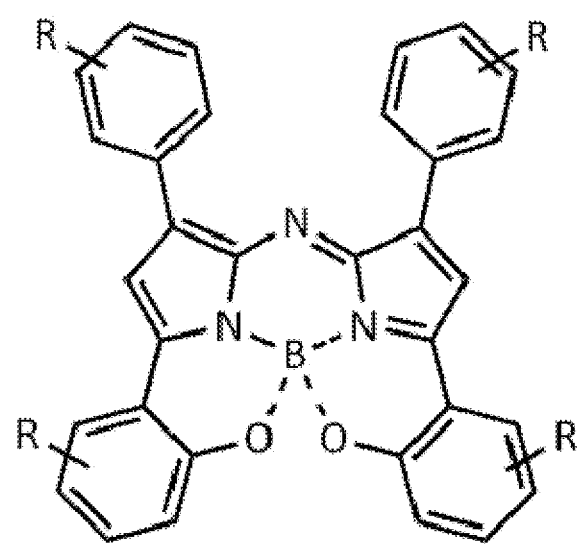
FIG. 1E illustrates a general structure of a B,O-chelated azadipyrromethene dye.

FIGS. 1A and 1B illustrate general boron dipyrromethene structures. FIG. 1C illustrates a general boron azadipyrromethene structure. FIG. 1D illustrates a general structure of conformationally restricted boron azadipyrromethenes. In FIG. 1D, the bridging ethylene moieties increase the planarity of the dye. The increased planarity can result in an increase in fluorescence efficiency and an increase in the red shift of the absorbance and emission maxima. FIG. 1E illustrates a general B,O-chelated azadipyrromethene structure. In FIGS. 1A-1E, each R may independently be hydrogen or any alkyl, branched alkyl, alkoxy, branched alkoxy, amino, alkylamino, dialkylamino, thiol, alkylthio, alkylester, alkyl amide, halide, or nitro group. Each R may be modified to alter solubility or spectral properties of dyes for selected purposes. For example, substitution of the phenyl groups at the 4-position of the pyrrole may allow tuning of fluorescence properties (e.g., absorbance and emission maxima) of the dye. In some cases, excitation wavelengths may range from about 550 nm to about 775 nm; emission wavelengths may range from about 570 nm to about 815 nm.

Azadipyrromethene and dipyrromethene dyes provide increased chemical stability, higher fluorescence efficiency, and improved solubility as compared to other petroleum markers. A higher fluorescence efficiency reduces the amount of marker necessary for detection. In addition, azadipyrromethene or dipyrromethene dyes are relatively insensitive to solvent polarity. As such, these markers may be used and detected quantitatively in fuels that contain oxygenates, such as ethanol, methyl t-butyl ether (MTBE), methanol (MeOH), gasoline grade t-butanol (GTBA), and the like. Other classes of near infrared fluorophores, such as phthalocyanines, cyanine, and quinone dyes, undergo spectral changes in solvents of different polarity. These spectral changes, which may include bathochromic/hypsochromic spectral shifts, changes in fluorescence quantum efficiency, and the like, make it difficult to quantify the amount of marker present.

In some embodiments, an azadipyrromethene dye, a dipyrromethene dye, or any combination thereof may be used as quantitative markers to detect dilution (i.e., decreased concentration of the marker) caused by mixing, for example, a first fuel with a desired concentration of the quantitative marker and a second fuel with a lower concentration of the quantitative marker. In some cases, as little as 5% or as little as 1% dilution is detectable with the use of azadipyrromethene and dipyrromethene dyes as markers.

In certain embodiments, an azadipyrromethene dye, a dipyrromethene dye, or any combination thereof may be added as a marker to a potential adulterant (e.g., a solvent, industrial solvent, or other hydrocarbon). If the adulterant is combined with a fuel, detection of the azadipyrromethene or dipyrromethene dye may be used to confirm the presence of the adulterant in the fuel. In some cases, as little as 5% or as little as 1% dilution of a fuel with an adulterant is detectable with the use of azadipyrromethene and dipyrromethene dyes as markers. In an example, a quantity of kerosene is marked with an azadipyrromethene dye, a dipyrromethene dye, or any combination thereof. If a fuel (e.g., diesel fuel) is adulterated with some of the marked kerosene, the presence of the kerosene in the diesel fuel may be detected based on the presence of the marker.

Testing for the presence of quantitative markers in fuel may be achieved on-site for rapid determination, or in a laboratory. In some cases, a concentration of an azadipyrromethene and dipyrromethene dye in a fuel is assessed by absorption spectroscopy with ultraviolet, visible, or infrared radiation, in which absorption of radiation by the sample is proportional to the concentration of the marker in the sample. The use and detection of quantitative markers is described in U.S. Pat. No. 5,525,516, which is incorporated herein by reference. In some cases, a concentration of an azadipyrromethene and dipyrromethene dye in a fuel is assessed by fluorescence spectroscopy, as described, for example, in U.S. Patent Application Publication No. 2008/0118982, which is incorporated herein by reference. Light in the visible range of the electromagnetic spectra may be used to excite fluorescence in the dye, which is subsequently detected in, for example, the visible or near infrared range.

Figure 2:
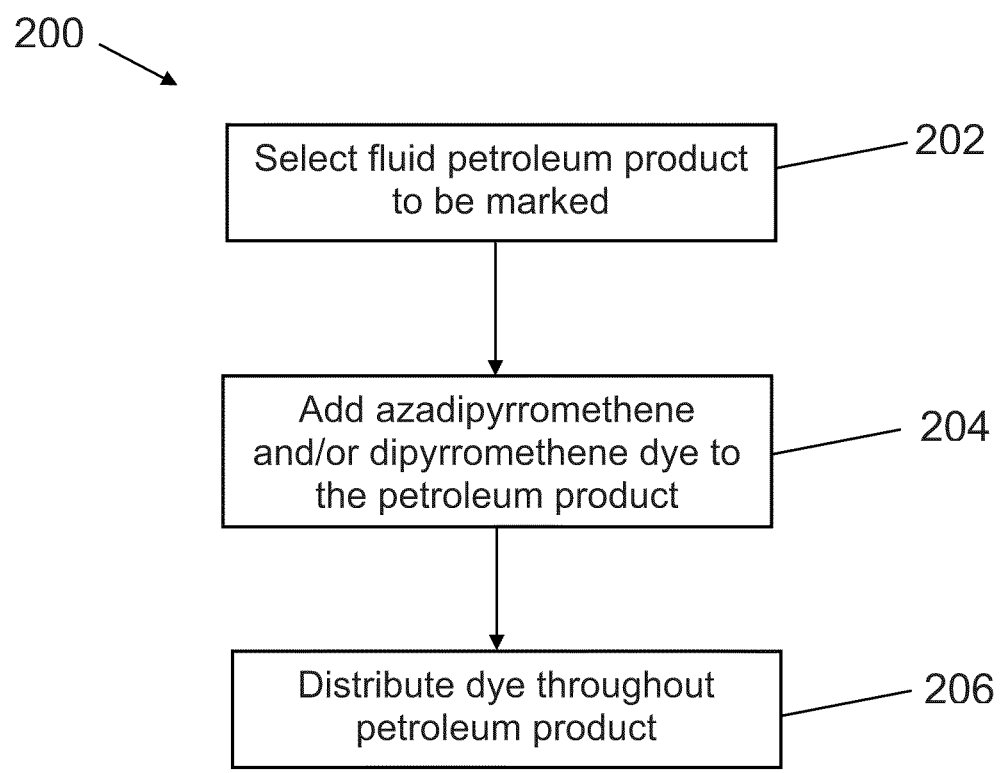
FIG. 2 illustrates a flow chart of a method of marking a fluid petroleum product with an azadipyrromethene and/or dipyrromethene dye.

FIG. 2 illustrates a method 200 of marking a fluid petroleum product with an azadipyrromethene and/or dipyrromethene dye and subsequently detecting the dye in the petroleum product. In step 202, a fluid petroleum product to be marked is selected. The petroleum product may be a fuel including an oxygenate. In step 204, an azadipyrromethene dye, a dipyrromethene dye, or any combination thereof is added to the fluid petroleum product selected in step 202. The petroleum product may be held in a container for transportation or storage, in a pipeline, or any other arrangement. The dye may be added to achieve a concentration between about 0.1 ppb and about 10,000 ppb in the petroleum product. For example, the dye may be added to achieve a concentration between about 0.1 ppb and about 10 ppb, between about 10 ppb and about 100 ppb, between about 100 ppb and about 500 ppb, or between about 500 ppb and about 1000 ppb. In step 206, the petroleum product may be agitated to distribute the dye in the product. In some cases, agitation may occur incidentally, such as during transportation of the product.

Figure 3:
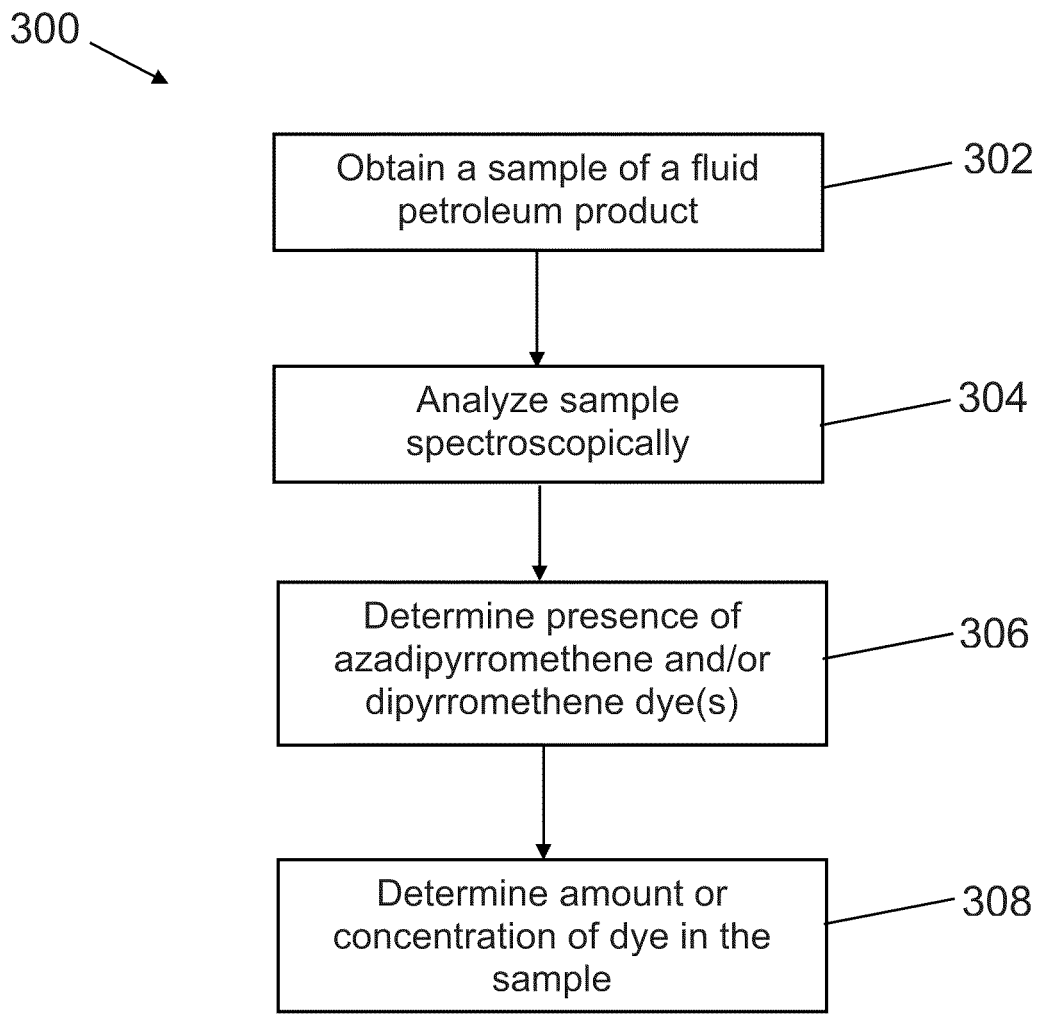
FIG. 3 illustrates a flow chart of a method of detecting an azadipyrromethene and/or dipyrromethene dye in a fluid petroleum product.

FIG. 3 illustrates a method 300 of testing a fluid petroleum product for the presence of an azadipyrromethene dye, a dipyrromethene dye, or a combination thereof, and subsequently detecting the dye in the petroleum product. In step 302, a sample of a petroleum product is obtained. In step 304, the sample is subjected to analysis by absorbance spectroscopy, fluorescence spectroscopy, or a combination thereof. In step 306, the presence of an azadipyrromethene dye, a dipyrromethene dye, or a combination thereof is determined, for example, by the presence of a particular peak or band in the spectrum. In step 308, the spectroscopic data may be analyzed to determine an amount or concentration of the dye in the sample, and thus in the petroleum product.

The dye can be detected by a response of the dye. For example, the response can be an emission from the dye, an absorbance by the dye, or an emission from a reaction product formed by reacting the dye with another compound.

Figure 4:
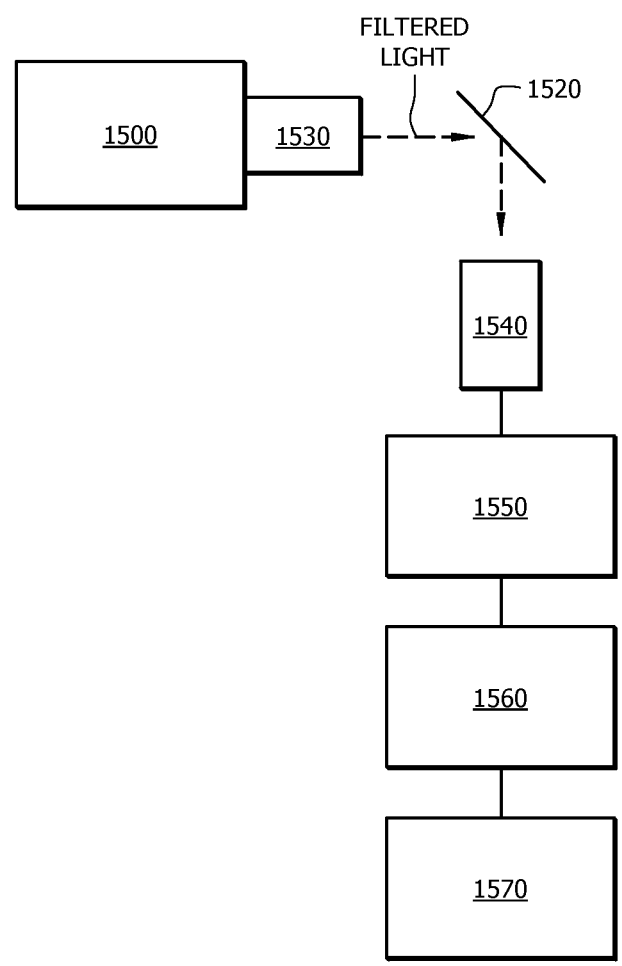
FIG. 4 illustrates a spectrometer.

For example, FIG. 4 illustrates an apparatus useful for detecting, identifying, and/or quantifying the dye in a marked petroleum product. The apparatus includes a light source 1500, which may emit radiation in the visible and near infrared region. The light source 1500 may be a multi-wavelength light source or it may be a tuned laser having a narrow band of wavelengths. After passing through a wavelength selector 1530 (e.g., monochromator or interference filter), the light from light source 1500 illuminates the dye or dyes in the marked petroleum product, which may be placed on a stage 1520. A second wavelength selector 1540 and photodetector 1550 may be placed at a 90 degree angle (relative to the direction of light shining on stage 1520). Having the light source 1500, wavelength selectors 1530 and 1540, and photodetector 1550 arranged on two sides of a triangle (as shown), can minimize scattered light entering the detector. After passing through the photodetector 1550, the light may pass through an amplifier 1560, and then onto a digital muiltimeter 1570 for detection. The output of the digital multimeter may be coupled to a computer and a display (not shown) to provide for numerical and graphical indication of the amount of luminous flux at the predetermined wavelength emitted and/or absorbed by the dye or dyes in the petroleum products.

Figure 5:
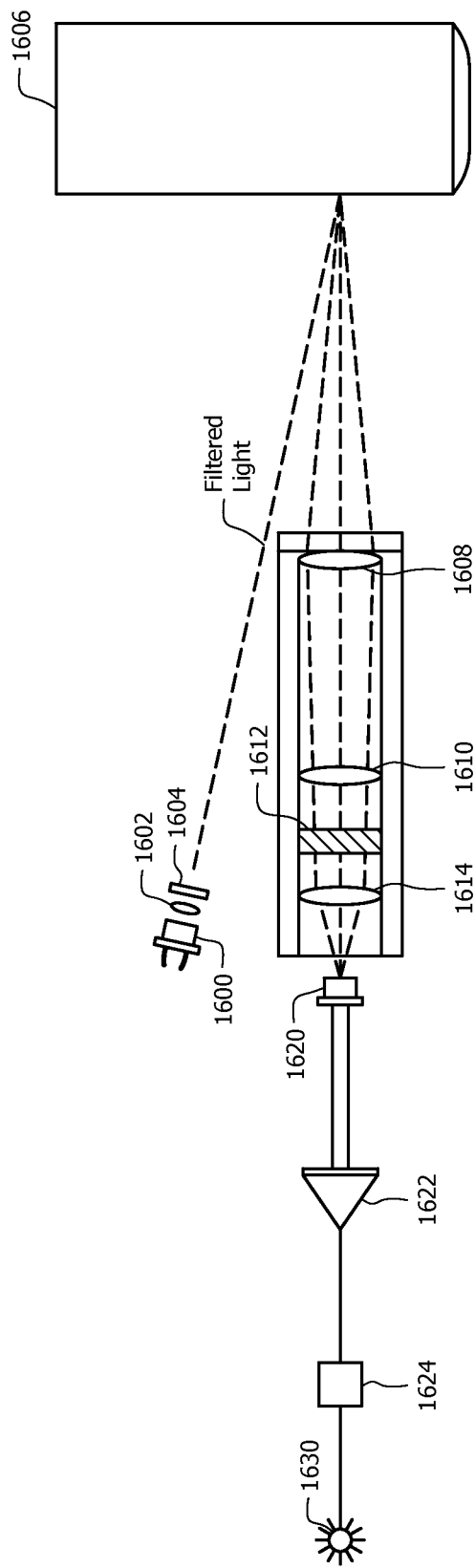
FIG. 5 illustrates a spectrometer utilizing a laser diode light source and an LED indicator.

FIG. 5 illustrates another apparatus useful for detecting, identifying, and/or quantifying the dye in a marked petroleum product. The apparatus has a laser diode light source 1600, which may emit radiation in the near infrared region. The light from the laser diode light source 1600 may be collimated through a collimating lens 1602, may pass through a filter 1604, and may then illuminate the marked petroleum product 1606. Thereafter, the light may pass through a focusing lens 1608, followed by a first compressing lens 1610, a filter 1612, and then a second compressing lens 1614. The angle between the light striking the petroleum product 1606 and the focusing lens, compressing lenses and filter may define an angle of about 30 degrees or less, which tends to minimize scattered light. After passing through the second compressing lens, the light may strike a photodetector 1620. The signal from the photodetector 1620 may be amplified with a current-to-voltage converter 1622. The output from the amplifier 1622 may then be detected by a threshold detector 1624, which may be configured to minimize any interference from unmarked materials. Furthermore, the presence of a dye or dyes may be indicated by a light-emitting diode (LED) indicator 1630.

In some embodiments, the emission and/or the absorbance is quantified to determine the concentration of the dye or dyes. For example, the absorbance can be quantified by integration of the detected signal, and then comparing the integrated signal to a calibration curve. In some embodiments, a full spectrum is obtained of the dye or dyes to obtain a fingerprint of the dye or dyes. In some embodiments, at least two dyes are utilized and a ratio of their emission and/or absorbance is used to determine authenticity of a sample.

In some embodiments, emission and/or absorbance data is collected on the dye or dyes, and then the data collected is compared to data for a library of dyes to identify a source of the marked product.

EXAMPLES

Figure 6:
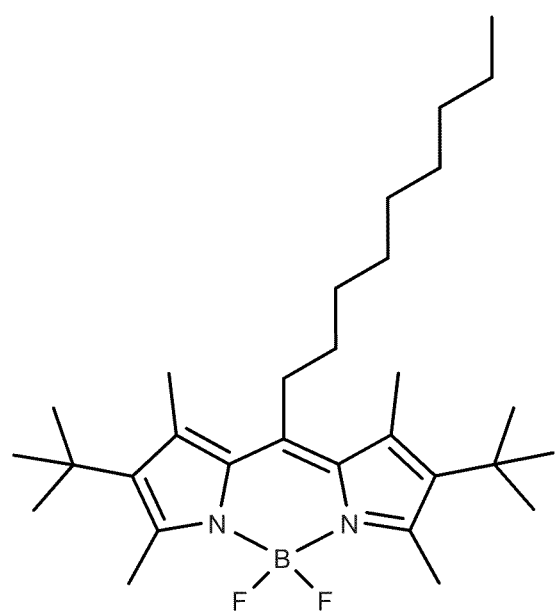
FIG. 6 illustrates an example of a $BF_2$ chelated dipyrromethene dye.

FIG. 6 illustrates an example of a BF$_2$ chelated dipyrromethene dye (DYE 1: BF$_2$ chelated 2,6-di-tert-butyl-8-nonyl-1,3,5,7-tetramethylpyrromethene).

Figure 7:
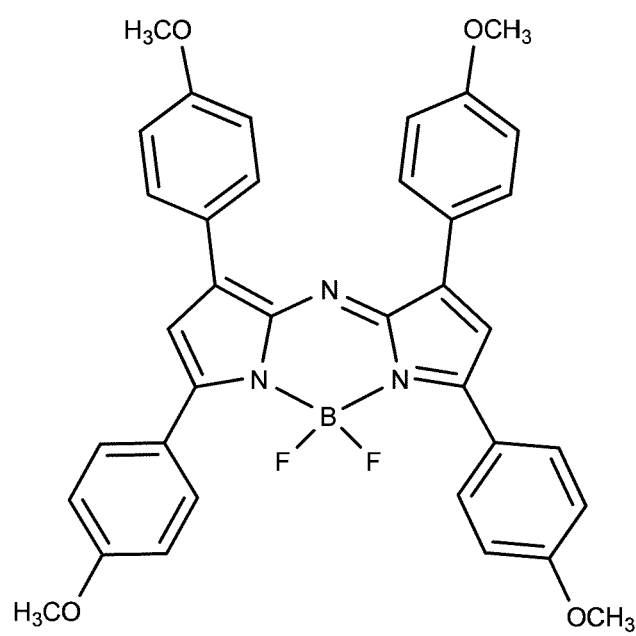
FIG. 7 illustrates an example of an azadipyrromethene dye.

FIG. 7 illustrates an example of an azadipyrromethene dye (DYE 2: BF$_2$ chelated [3,5-di-(4-methoxyphenyl)-5-phenyl-1H-pyrrol-2-yl]-[3-(4-methoxyphenyl)-5-phenylpyrrol-2-ylidene]amine).

Figure 8:
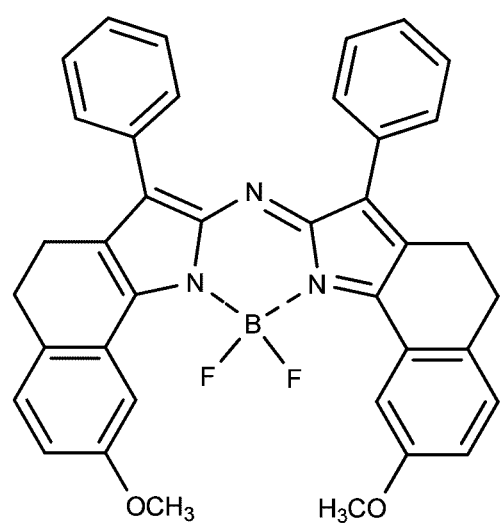
FIG. 8 illustrates an example of a conformationally restrained azadipyrromethene dye.

FIG. 8 illustrates an example of a conformationally restrained azadipyrromethene dye (DYE 3: BF$_2$ chelated [8-methoxy-3-phenyl-4,5-dihydro-1H-benzo[g]pyrrol-2-yl]-[8-methoxy-3-phenyl-4,5-dihydro-1H-benzo[g]pyrrol-2-ylidine]amine).

Figure 9:
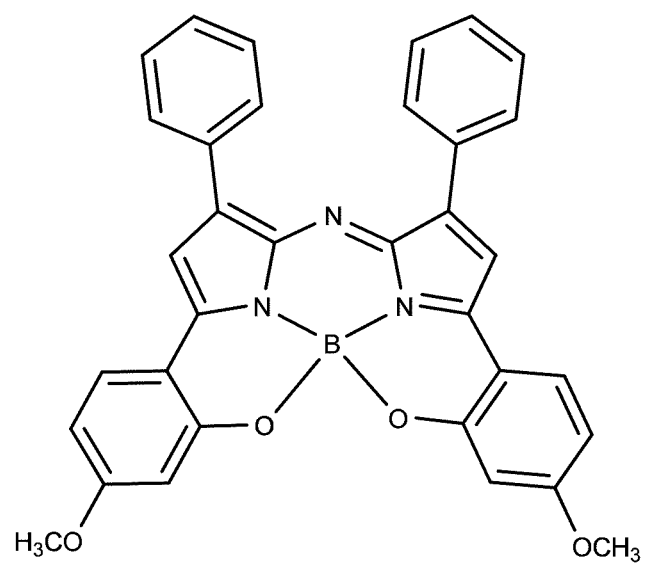
FIG. 9 illustrates an example of a B,O chelated azadipyrromethene dye.

FIG. 9 illustrates an example of a B,O chelated azadipyrromethene dye (DYE 4: boron chleated[5-(2-hydroxy-4-methoxyphenyl)-3-phenyl-1H-pyrrol-2-yl]-[5-(2-hydroxy-4-methoxyphenyl)-3-phenylpyrrol-2-ylidene]amine).

Figure 10:
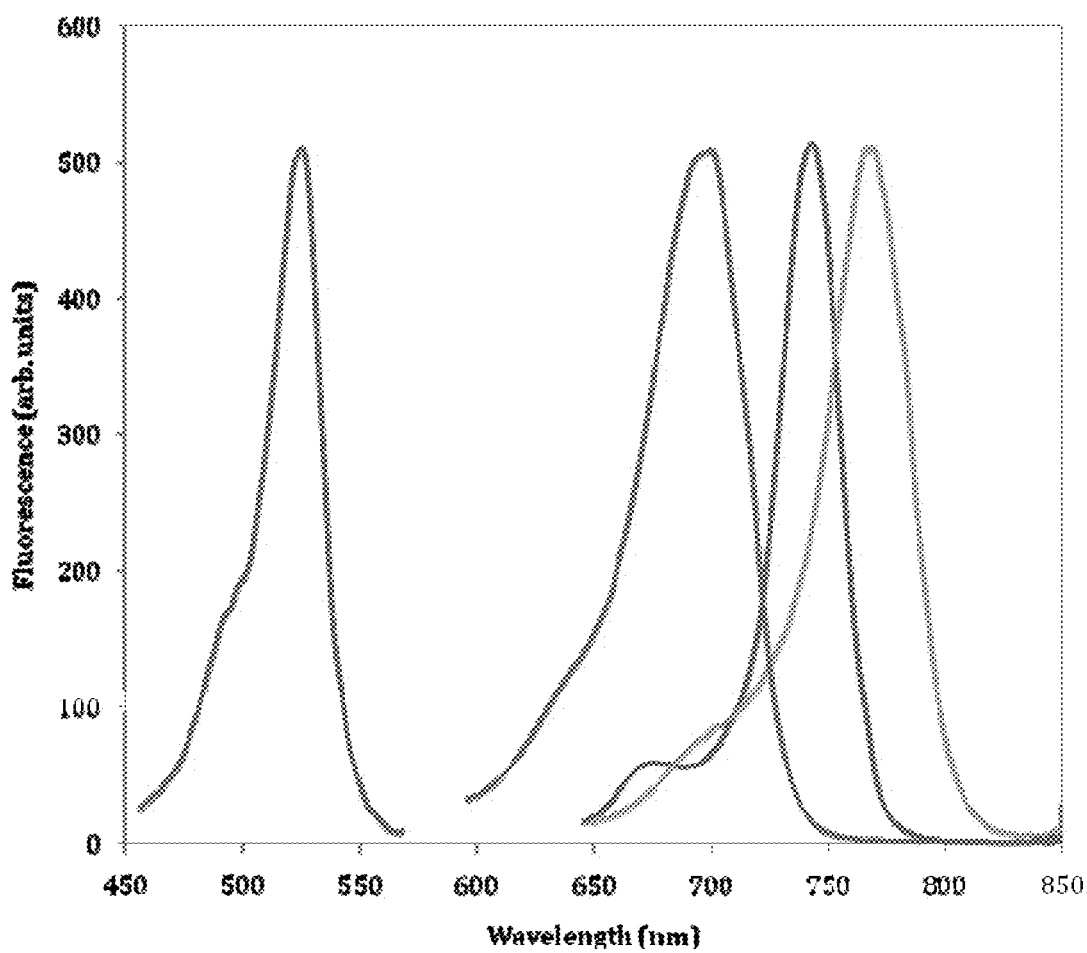
FIG. 10 illustrates fluorescence excitation spectra of the dyes illustrated in FIGS. 6-9.
Figure 11:
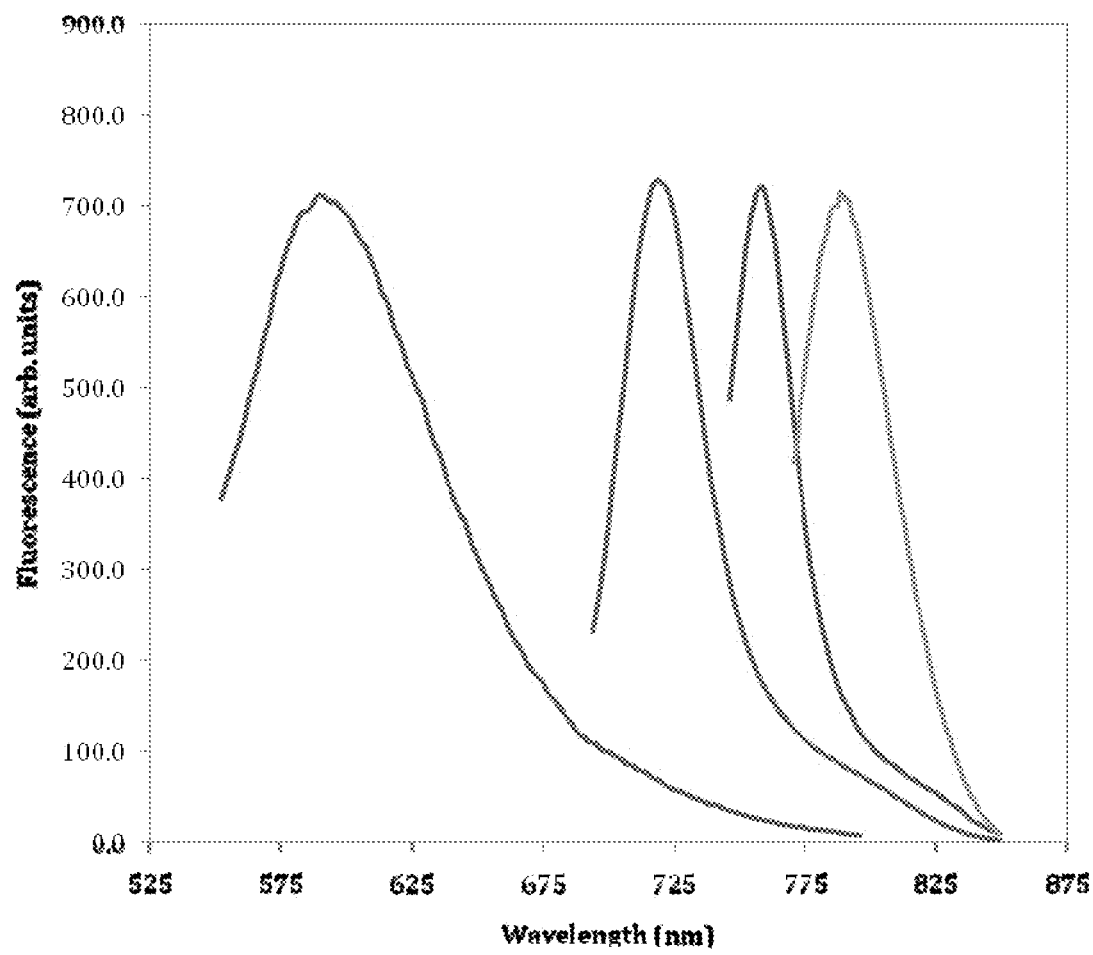
FIG. 11 illustrates fluorescence emission spectra of the dyes illustrated in FIGS. 6-9.

Samples of DYES 1-4 were prepared in toluene at a concentration of 100 ppm. For fluorescence analysis, the samples were diluted with gasoline to a concentration of 500 ppb. Fluorescence spectra shown in FIGS. 10 and 11 were obtained on a Varian Cary Eclipse Fluorescence Spectrophotometer in 1 cm quartz cuvettes. FIG. 10 shows fluorescence excitation spectra of the 500 ppb samples of DYES 1-4, with maxima at about 525 nm, 695 nm, 745 nm, and 760 nm, respectively. FIG. 11 shows fluorescence emission spectra of the 500 ppb samples of DYES 1-4, with maxima at about 585 nm, 725 nm, 760 nm, and 790 nm, respectively.

A number of embodiments of the invention have been described. Nevertheless, it will be understood that various modifications may be made without departing from the spirit and scope of the invention.

What is claimed is:

1. A marked petroleum fuel comprising a fuel additive, a mixture of a fluid petroleum fuel and a marker, wherein the marker consists of a single dye, and wherein the dye is selected from the group consisting of halogenated-boron dipyrromethene dyes characterized by the following structure:

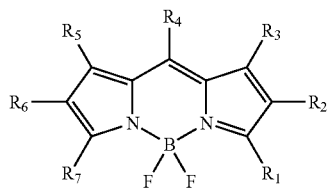

where each R is independently selected from the group consisting of hydrogen, an alkyl group, a branched alkyl group, an alkoxy group, a branched alkoxy group, an amino group, an alkylamino group, a dialkylamino group, a thiol group, an alkylthio group, an alkylester group, an alkyl amide group, a halide group, and a nitro group, wherein the dye is characterized by a resistance to solvatochromatic-based shifting of a fluorescence response when mixed with the petroleum fuel comprising a fuel additive and wherein the dye is present in an amount of from about 0.1 ppb to about 10,000 ppb.

2. The marked petroleum fuel of claim 1, wherein the petroleum fuel is selected from the group consisting of gasoline diesel fuel, biodiesel fuel, kerosene, liquefied petroleum gas, ethanol, and any combination thereof.

3. The marked petroleum fuel of claim 1, wherein the fuel additive is an oxygenate.

4. A method of detecting a couterfeit or adulterated petroleum product, the method comprising:
spectroscopically analyzing a portion of the petroleum product for the presence of a marker, wherein the marker consists of a single dye, and wherein the single dye is a halogenated-boron dipyrromethene dyes characterized by the following structure:

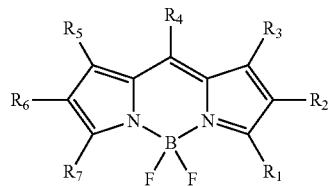

where each R is independently selected from the group consisting of hydrogen, an alkyl group, a branched alkyl group, an alkoxy group, a branched alkoxy group, an amino group, an alkylamino group, a dialkylamino group, a thiol group, an alkylthio group, an alkylester group, an alkyl amide group, a halide group, and a nitro group;
determining a concentration of the marker present in the portion of the petroleum product; and
identifying the petroleum product as counterfeit, adulterated or authentic as a function of the determined concentration of the marker wherein the petroleum product is a petroleum fuel comprising a fuel additive, wherein the dye is characterized by a resistance to solvatochromatic-based shifting of a fluorescence response when mixed with the petroleum fuel comprising a fuel additive and wherein the dye is present in an amount of from about 0.1 ppb to about 10,000 ppb.

5. The method of claim 4, wherein the petroleum product comprises an oxygenate.

6. The method of claim 5, wherein the oxygenate is selected from the group consisting of methanol, ethanol, gasoline grade t-butanol, methyl t-butyl ether, and any combination thereof.

7. The method of claim 4, wherein the identifying step further comprises comparing the determined concentration with a target concentration of the marker.

8. A method of detecting an adulterated petroleum product comprising spectroscopically analyzing a portion of the petroleum product for a presence of a marker, wherein the marker consists of a single dye, and wherein the single dye is a a halogenated-boron dipyrromethene dyes characterized by the following structure:

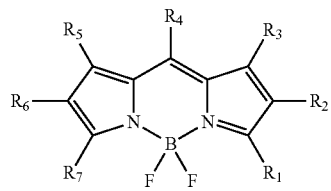

where each R is independently selected from the group consisting of hydrogen, an alkyl group, a branched alkyl group, an alkoxy group, a branched alkoxy group, an amino group, an alkylamino group, a dialkylamino group, a thiol group, an alkylthio group, an alkylester group, an alkyl amide group, a halide group, and a nitro group, wherein the presence of a marker is indicative of adulteration of the petroleum product, wherein the petroleum product is a petroleum fuel, wherein the dye is characterized by a resistance to solvatochromatic-based shifting of a fluorescence response when mixed with the petroleum fuel comprising a fuel additive and wherein the dye is present in an amount of from about 0.1 ppb to about 10,000 ppb.

9. The method of claim 8, further comprising, previous to the spectroscopically analyzing the portion of the petroleum product, mixing the halogenated-boron dipyrromethene dye with the petroleum product.

10. The method of claim 8, wherein the fuel additive comprises an oxygenate.

11. The method of claim 10, wherein the oxygenate is selected from the group consisting of methanol, ethanol, gasoline grade t-butanol, methyl t-butyl ether, and any combination thereof, and wherein the marker is characterized by a resistance to solvatochromatic-based shifting of its fluorescent response when mixed with the petroleum fuel comprising the oxygenate.

12. A method comprising adding a covert dye to a petroleum fuel comprising an oxygenate, wherein the covert dye consists of a single dye, and wherein the single dye is a halogenated-boron dipyrromethene dye characterized by the following structure:

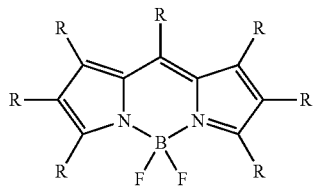

where each R is independently selected from a hydrogen, an alkyl group, a branched alkyl group, an alkoxy group, a branched alkoxy group, an amino group, an alkylamino group, a dialkylamino group, a thiol group, an alkylthio group, an alkylester group, an alkyl amide group, a halide group and a nitro group wherein the convert dye is characterized by a resistance to solvatochromatic-based shifting of its fluorescent response when mixed with the petroleum fuel comprising the oxygenate and wherein the dye is present in an amount of from about 0.1 ppb to about 10,000 ppb.

13. The method of claim 12 further comprising identifying the petroleum fuel by spectroscopically analyzing a portion of the petroleum fuel for the presence of the covert dye.

14. The method of claim 12 wherein the oxygenate is selected from the group consisting of methanol, ethanol, gasoline grade t-butanol, methyl t-butyl ether, and any combination thereof.

15. The method of claim 12 further comprising:
determining a concentration of the covert dye present in a portion of the petroleum fuel; and
identifying the petroleum fuel as counterfeit, adulterated or authentic based on the determined concentration of the covert dye.

16. The method of claim 15 wherein the determining the concentration of the covert dye present in the portion of the petroleum fuel spectroscopically analyzes the portion of the petroleum fuel for the presence of the covert dye.

17. The method of claim 4 wherein spectroscopically analyzing a portion of the petroleum product comprises a direct-read measurement.

18. The method of claim 8 wherein spectroscopically analyzing a portion of the petroleum product comprises a direct-read measurement.

19. The method of claim 12 further comprising spectroscopically analyzing a portion of the petroleum fuel utilizing a direct-read measurement.

20. The method of claim 1 wherein the dye is present in an amount of from about 500 ppb to about 10,000 ppb.

21. The method of claim 4 wherein the dye is present in an amount of from about 500 ppb to about 10,000 ppb.

22. The method of claim 8, wherein the dye is present in an amount of from about 500 ppb to about 10,000 ppb.

23. The method of claim 12 wherein the dye is present in an amount of from about 500 ppb to about 10,000 ppb.

24. The method of claim 1 wherein the dye is present in an amount of from about 0.1 ppb to about 1,000 ppb.

25. The method of claim 4 wherein the dye is present in an amount of from about 0.1 ppb to about 1,000 ppb.

26. The method of claim 1 wherein the dye has an emission wavelength ranging from about 570 nm to about 815 nm.

* * * * *

UNITED STATES PATENT AND TRADEMARK OFFICE
CERTIFICATE OF CORRECTION

PATENT NO.        : 9,222,043 B2
APPLICATION NO.   : 12/885741
DATED             : December 29, 2015
INVENTOR(S)       : Philip B. Forshee, Greg R. Hundt and Jeffrey L. Conroy It is certified that error appears in the above-identified patent and that said Letters Patent is hereby corrected as shown below:

In the Claims:

Column 6, Claim 4, Line 12, replace "dipyrromethene dyes" with --dipyrromethene dye--.
Column 6, Claim 8, Line 55, replace "a a halogenated-boron dipyrromethene dyes" with --a halogenated-boron dipyrromethene dye--.
Column 8, Claim 12, Line 2, replace "convert dye" with --covert dye--.

Signed and Sealed this
Fifteenth Day of March, 2016

Michelle K. Lee
*Director of the United States Patent and Trademark Office*